United States Patent
Crandall (12)

(10) Patent No.: US 6,306,383 B1
(45) Date of Patent: Oct. 23, 2001

(54) METHOD FOR TOPICAL TREATMENT OF SCARS WITH PROTEIN KINASE C INHIBITORS

(75) Inventor: Wilson T Crandall, P.O. Box 346, Verona, VA (US) 24482

(73) Assignee: Wilson T Crandall, Defiance, VA (US)

( * ) Notice: Subject to any disclaimer, the term of this patent is extended or adjusted under 35 U.S.C. 154(b) by 0 days.

(21) Appl. No.: 09/395,511

(22) Filed: Aug. 31, 2001

Related U.S. Application Data

(60) Provisional application No. 60/100,530, filed on Sep. 16, 1998, provisional application No. 60/114,813, filed on Jan. 6, 1999, and provisional application No. 60/123,594, filed on Mar. 10, 1999.

(51) Int. Cl.$^7$ .......................... A61K 31/74; A61K 45/00; A61K 9/127; A01N 65/00
(52) U.S. Cl. ........................ 424/78.06; 424/78.02; 424/78.03; 424/283.1; 424/450; 424/725
(58) Field of Search ...................... 424/401, 725, 424/78.02, 78.03, 78.06, 283.1, 450; 514/847, 859, 886, 863, 944, 844

(56) References Cited

U.S. PATENT DOCUMENTS

| | | | | |
|---|---|---|---|---|
| 5,552,162 | * | 9/1996 | Lee | 424/646 |
| 5,925,376 | * | 6/1999 | Heng | 424/451 |
| 6,019,988 | * | 2/2000 | Parab et al. | 424/400 |
| 6,045,827 | * | 4/2000 | Russell | 424/485 |

FOREIGN PATENT DOCUMENTS

WO 97/40830 * 11/1997 (WO).
WO 99/29293 * 6/1999 (WO).

OTHER PUBLICATIONS

Scartazzini et al., Organogels From Lecithins; 1988, J. Phys. Chem, 92, pp. 829–833.*
Luisi et al. Organogels From Water–In–Oil Microemulsions; 1990, Colloid & Polymer Science, 268, pp. 356–374.*
Willimann et al. Lecithin Organogel as Matrix for Transdermal Transport of Drugs; Journal of Pharmaceutical Sciences vol. 81, No. 9 pp.871–874, Sep. 1992.*

* cited by examiner

Primary Examiner—Jon P. Weber
Assistant Examiner—Patricia Patten

(57) ABSTRACT

This invention relates to the topical treatment of keloids, hypertrophic scars and burn scars by the use of a selected protein kinase c inhibitor and an effective penetrating agent selected from lecithin organogel or poloxamer 407 lecithin organogel. The protein kinase c inhibitors may be selected from sphingosine, sphinganine, phytosphingosine, N-Acetylsphingosine, N-Hexanoylsphingosine, N-Octanoylsphingosine, curcumin, tetrahydrocurcumin, curcuminoids or apigenin.

10 Claims, No Drawings

METHOD FOR TOPICAL TREATMENT OF SCARS WITH PROTEIN KINASE C INHIBITORS

PRIOR RELATED APPLICATIONS

This application is a continuation of U.S. provisional applications Ser. Nos. 60/100,530, 60/114,813 and 60/123,594 filed on Sep. 16, 1998, Jan. 6, 1999 and Mar. 10, 1999, respectively.

TECHNICAL FIELD OF THE INVENTION

The present invention is related to a process and composition for topically inhibiting Protein Kinase C. More particularly, the present invention relates to topically applying the composition disclosed herein in order to treat the affected skin or underlying structures of humans and animals. Protein kinase C inhibitors have been shown effective in vitro and in a limited fashion orally, but not efficacious when used topically. What is needed is a topical composition which is safe and cost effective.

BACKGROUND OF THE INVENTION

Mukhtar in Pharmacology of the Skin describes the communication between cells as being mediated by different biomolecules, such as hormones. These so called primary messengers bind to specific receptors on the cell surface. The binding of a primary messenger to its receptor conveys a certain information to the cell which is subsequently transduced through the membrane by a chain of signaling. This process involves various membrane structures and leads to the activation of an enzyme located at the intracellular side of the membrane. The stimulated enzyme generates a second messenger which evokes the cellular response; in most cases, by the activation of other enzymes. By these steps, the initial extracellular signal is converted into an intracellular signal. This process is called signal transduction.

The inositide cascade represents one of several signals transducing pathways. In its course, two second messengers, diacylglycerol (DG) and inositol triphosphate (IP 3)., are released. DG remains in the membrane and activates protein kinase C (PKC). IP 3 acts by releasing calcium ions from their intracellular stores. The calcium ions subsequently evoke the cellular response, mainly by activating a protein kinase (PKC)

Protein kinases regulate cellular responses by phosphorylation of substrate proteins (eg. receptors or enzymes) and thereby alter their state of activity. In the case of the inositide cascade, PKC mainly performs this reaction. Sphingosine dose-dependently inhibits PKC, but also binds to calmodulin (CaM) function and therefore inhibits CaM function. Keratinocyte intercellular adhesion molecule-1 (ICAM-1) is thought to be involved in dermal lymphocyte infiltration. The PKC activating phorbol ester, PMA has been reported to induce the expression of ICAM-1 in normal human keratinocytes. This effect can be blocked by a PKC inhibitor and suggests that PKC might play a regulatory role in ICAM-1 expression.

Psoriasis is characterized by a epidermal hyperproliferation and reduced cellular differentiation as well as inflammation. Experimental stimulation of PKC will produce a similar hyperproliferation. The release of reactive oxygen species (ROS) from human leucocytes represents an important part of the acute inflammation. Phorbol ester can induce the same cellular response and is mainly regulated by PKC. This pathway in psoriasis if stimulated by an activator of PKC, may account for epidermal inflammation.

PKC is known to function in cutaneous tumor promotion in that it represents the major cellular receptor for phorbol esters. PKC inhibitors like sphingosine inhibit phorbol ester-induced ornithine decarboxylase activity in the mouse skin.

SUMMARY OF THE INVENTION

The present invention provides a composition and easy to use therapeutic method for inhibiting PKC activity in the skin, muco-cutaneous junction and underlying structures, as well as the disease processes related to it. These processes include, but are not limited to psoriasis, psoriatic arthritis, tumor, cell mediated hyper immunity, seborrheic dermatitis, allergic & contact dermatitis, hypertrophic scar, keloid, carpal tunnel disease $2^{nd}$ to fibrosis, papilloma virus warts, vitiligo, solar elastosis, and any inflammatory conditions in the skin which involve PKC.

The present invention includes a composition for topical treatment of the effects of PKC activity as a second messenger wherein the molecule or molecules are selected from the group consisting of phytosphingosine, sphingosine, sphinganine, curcumin, tetrahydrocurcumin, curcumin analogues, apigenin, hypericin, N-Acetylsphingosine, N-Hexanoylsphingosine, and N-Octanoylsphingosine or W-7 analogue combined with delivery vehicles and penetrating agents optionally containing lecithin, unhydrogenated or hydrogenated, lecithin organogel, Pluronic 127 lecithin organogel. Therapeutically effective amounts of phytosphingosine may be combined at concentrations of 0.01 g to 5 g per 100 grams of formulation for topical application of the composition of this invention. Optionally 0.01 g to 5 g tetrahydrocurcumin may be used by itself or in combination with the phytosphingosine or another PKC inhibitor

DETAILED DESCRIPTION OF THE INVENTION

PKC activity in the skin and the disease processes related to it, include psoriasis, tumor, hypertrophic scar & keloid, cell mediated hyperimmunity, atopy & contact dermatitis, and other processes.

PKC activity in the joint including rheumatoid arthritis.

The term patient refers to mammals, especially humans and animals.

A preferred phospholipid for use in the present invention is phosphatidylcholine, unhydrogenated or hydrogenated, also known as lecithin. Stedman's medical dictionary ($21^{st}$ ed., pg. 879) defines lecithin as any group of phospholipids which upon hydrolysis yield 2 fatty acids molecules and a molecule each of glycerophosphoric acid and choline. There are several varieties of lecithin, Soybean lecithin is a preferred lecithin and is the most economical. Lecithins are also found in nervous tissue, hepatic tissue, cardiac tissue and egg yolks. It is there fore understood that any reference to lecithin or phosphatidylcholine is intended to include any combination of lecithin-like phospho-lipid compounds as is well known in the art. Examples of other phospholipids which can be used in accordance with the present invention include phosphatidylethanolamine, phosphatidylserine, phosphatidyinositol, and phosphatidic acid. A mixture of any of the above phospholipids maybe used in the present invention and are present in natural soy lecithins. A hydrogenated lecithin may also be employed which obviates the problem with oxidation.

A preferred penetrating agent and delivery vehicle is lecithin organogel which is a combination of lecithin, organic solvent such as ethanol and water. Lecithin organogels have described as vehicles that are useful in facilitating the delivery of low molecular weight compounds transdermally (Williman et al, Journal of Pharmaceutical Sciences 81:871–874 (1992) which is incorporated herein by reference). The lecithin organogels are obtained by adding small amounts of water to a solution of lecithin in organic solvent. Generally, lecithin organogels are prepared at room temperature by first dissolving lecithin in an organic solvent such as ethanol, isopropyl palmitate or isopropyl myristate and then adding enough water while stirring to obtain the desired gel. Preparation of a variety of lecithin gels, all of which are appropriate in practicing the invention, are described in Scartazzini, et al Journal of Physical Chemistry 92:829–833, 1988, and Luisi, P. L. et al Colloid and Polymer Science 268;356–374. 1990, both of which are incorporated herein by reference in their entirety. The lecithin organogel preferably comprises 1:1 to 1.5:5 (weight/volume) of Phosphlipon 90(PC) (American Lecithin, Oxford, Conn.) ethanol (1 g:1 ml). Water is added to form the desired gel. Other penetrating agents may be used in the composition of the present invention. The composition according to the present invention can be in the form of lotions, salves, creams, ointments, liposomes, giant micelles, and salves.

A gelling agent optionally may be added to the formulation. Gelling agents that are suitable include, but are not limited to Pluronic lecithin organogel, cellulose ethers, alginates, polyacrylates (carbomers), carboxyvinyl polymer, bentonite, gelatin, tragcanth, polyvinylpyrrolidone, polyvinyl alcohol, and polyoxyethylene/polyoxypropylene block copolymers.

The term "Pluronic" refers to a polxamer compounds and are sold collectively under the trademark PLURONIC (BASF, Parsippany, N.J.) PLURONIC F-127 (PL 127) corresponds to poloxamer 407, a polyoxypropylene-polyoxyethylene block copolymer described by Schmolka in the Journal of Biomedical Materials Research 6:571–582. 1972. Other Pluronics maybe used in the present invention. As used in this application, the terms PLURONIC organogel, poloxamer organogel, and polyoxyethylene/polyoxypropylene organogel are synoymous.

The term "pharmacologically active agent" relates to any chemical material or compound suitable for topical administration which includes any desired local effect on animal or human tissue contacted therewith.

By the term "therapeutically effective amount" of a molecule, drug or pharmacologically active agent is meant a nontoxic but sufficient amount to provide the desired therapeutic effect.

The "enhanced penetration" caused by compositions of this invention as used in topical application with this method, means increased penetration into the skin, and is achieved with compounds such as lecithin organogel, poloxamer lecithin organogel or poloxamer phospholipid. These include PC, phosphatidylethanolamine, phosphatidylserine, phosphatidylinositol and phosphatidic acid in a unhydrogenated or hydrogenated form optionally combined with Pluronic 127, ethoxy dyglycol, ethanol or cholesterol. Enhanced penetration can be observed in many known to those skilled in the art.

The present invention optionally includes lecithin organogel in combination with an approximately 16%–98% solution of Pluronic F-127 (BASF, Parsippany, N.J.), otherwise known as poloxamer 407, in ratio of approximately, N.J.), in a ratio of 1:4 Other Pluronics may be used in the present invention.

Solvents used in the preparation of a variety of gels, including lecithin gels, all of which are appropriate in practicing the present invention, are described in Scartazzini, et al, Journal of Physical Chemistry 92: 829–833, and Luisi. P. L., et al Colloid and Polymer Science 268: 356–374. 1990, both of which are incorporated herein by reference in their entirety and may be referred to.

1 nM Disodium edetate is added to the gel so as to minimize auto oxidation. Other antioxidants which maybe used are vitamin E, vitamin C, (ascorbyl palmitate) green tea, grape seed extract, or kogic acid.

EXAMPLE 1
Treatment of a Disseminated Cutaneous Tumor in a White Rat 3 grams of Phosphal 75 SA (American Lecithin, Oxford, Conn.) was heated to 70 C. 150 mg of phytosphingosine was then added in 3 ml of ethanol to the lecithin. Stirring was continued until the dissolution was complete 9 ml of Pl 127 20% is added to the above when the temperature is 40 C. As the gel is forming 3 ml of water was stirred in.

The animal was treated every 8 hrs and a reduction of 50% was evident in the bigger tumors after only 24 hrs. Treatment continued for another 5 days after which the animal was clinically normal!

EXAMPLE 2
Treatment of Psoriasis 9 grams of Phosal 75 SA was heated to 70 C.. And 500 mg of phytosphingosine then added in 10 ml of ethanol to the lecithin. Stirring was continued until the dissolution was complete.

27 ml of Pl 127 20% was added to the above when the temperature reached 40 C.. As the gel is forming 10 ml of water was stirred in.

The plaques were treated 2–3xdaily and within 30 days the skin developed an almost normal texture and appearance.

This patient was asked to try a formulation with tetrahydrocurcumin on other areas of psoriasis.

5 grams of tetrahydrocurcumin was dissolved in 5 ml of ethanol and 7.5 g Phosal 75 SA and stirred at 60 C. Upon dissolution, 5 ml of deionized water was added with stirring. 65 ml of PL 127 25% is then added and mixed with power. Water qs to make 100 grams is then added.

A thin film of the formulation was applied to larger & thicker areas of psoriasis at the elbows. After 3 weeks the skin was all, but normal.

EXAMPLE 3
Treatment of Hypertrophic Scars

The formulation used in example 1 was applied to a 6 mm angry red scar on the dorsum of the hand twice daily. Within 36 hrs the scar was normal in volume and the color was much less intense.

A 35 year old woman had a facial scar on the right cheek dating since 18 months of age. The formulation used in example 1 was applied twice daily and photographs at 1 month show good improvement.

EXAMPLE 4
Treatment of a Seed Wart 1.5 g of phytosphingosine was dissolved in 5 ml of ethanol at 60 C. 7.5 g. 90s, American Lecithin co, Oxford, Conn. was added and stirred. Upon dissolution 5 ml of deionized water was added with additional stirring. 64 ml of Pl 127 25% was then added and mixed with power equipment. A wart on the foot (papilloma virus) for over 20 years was treated by applying a thin film of the formulation every 12 hrs. After 15 days the wart diminished in size and finally sloughed.

EXAMPLE 5

Treatment of Stretch Marks

A 33 year old mother of 3 had developed very prominent angry red/blue stretch marks which worsened after each birth. The scars were elevated and pruritic and the lady was extremely self conscious.

A 2% phytosphingosine gel was made as in example 1. A thin film was applied twice daily and a cessation of itching was reported after 3 days. Progress was evident by the $2^{nd}$ week and photos were taken 1&2 months. The intense discoloration subsided on 1 side and all but disappeared on the other. The scars were flat and appeared normal to the touch.

What is claimed is:

1. A method for treating a scar comprising the step of topically applying an effective amount of a Protein Kinase C inhibitor, wherein said Protein Kinase C inhibitor is selected from the group consisting of phytosphingosine, sphingosine, sphinganine, curcumin, tetrahydrocurcumin, curcuminoids, and apigenin and a pharmaceutically effective penetrating agent selected from the group consisting of lecithin organogel and poloxamer 407 lecithin organogel.

2. The method according to claim 1, wherein said scar is selected from the group consisting of hypertrophic, keloid and burn scar.

3. The method according to claim 1, wherein said pharmaceutically effective penetrating agent is in a form selected from the group consisting of gels, creams, sprays, salves, balms, liposomes, micelles and pads.

4. The method according to claim 1, wherein the protein kinase c inhibitor is phytosphingosine.

5. The method according to claim 1, wherein the protein kinase c inhibitor is sphingosine.

6. The method according to claim 1, wherein the protein kinase c inhibitor is sphinganine.

7. The method according to claim 1, wherein the protein kinase c inhibitor is curcumin.

8. The method according to claim 1, wherein the protein kinase c inhibitor is tetrahydrocurcumin.

9. The method according to claim 1, wherein the protein kinase c inhibitor is a curcuminoid.

10. The method according to claim 1, wherein the protein kinase c inhibitor is apigenin.

* * * * *